(12) United States Patent
Mulumudi et al.

(10) Patent No.: US 10,898,161 B2
(45) Date of Patent: Jan. 26, 2021

(54) ACOUSTIC COLLECTION SYSTEM FOR HANDHELD ELECTRONIC DEVICES

(71) Applicant: StratoScientific, Inc., Shoreline, WA (US)

(72) Inventors: Suman K. Mulumudi, Snohomish, WA (US); Mahesh S. Mulumudi, Snohomish, WA (US)

(73) Assignee: StratoScientific, Inc., Bothell, WA (US)

( * ) Notice: Subject to any disclaimer, the term of this patent is extended or adjusted under 35 U.S.C. 154(b) by 0 days.

(21) Appl. No.: 16/391,121

(22) Filed: Apr. 22, 2019

(65) Prior Publication Data

US 2019/0247009 A1    Aug. 15, 2019

Related U.S. Application Data

(63) Continuation of application No. 15/857,464, filed on Dec. 28, 2017, now Pat. No. 10,271,816, which is a continuation of application No. 15/627,313, filed on Jun. 19, 2017, now Pat. No. 9,855,019, which is a continuation of application No. 15/203,680, filed on Jul. 6, 2016, now Pat. No. 9,706,975, which is a
(Continued)

(51) Int. Cl.
| | | |
|---|---|---|
| *A61B 7/04* | (2006.01) |
| *H04R 1/46* | (2006.01) |
| *G10K 11/08* | (2006.01) |
| *G10K 11/00* | (2006.01) |
| *G10K 11/22* | (2006.01) |
| *H04R 3/04* | (2006.01) |

(52) U.S. Cl.
CPC .............. *A61B 7/04* (2013.01); *G10K 11/004* (2013.01); *G10K 11/08* (2013.01); *G10K 11/22* (2013.01); *H04R 1/46* (2013.01); *H04R 3/04* (2013.01); *H04R 2499/11* (2013.01)

(58) Field of Classification Search
None
See application file for complete search history.

(56) References Cited

U.S. PATENT DOCUMENTS

| | | |
|---|---|---|
| D214,002 S | 4/1969 | Machlup et al. |
| D269,295 S | 6/1983 | Bloom |
| | (Continued) | |

FOREIGN PATENT DOCUMENTS

| | | |
|---|---|---|
| KR | 10-2011-0047181 | 5/2011 |
| KR | 10-2013-0022141 | 3/2013 |
| | (Continued) | |

OTHER PUBLICATIONS

Brazilian Office Action dated Jun. 16, 2015, from application No. 3020140017020.
(Continued)

*Primary Examiner* — Paul W Huber
(74) *Attorney, Agent, or Firm* — Foley & Lardner LLP

(57) ABSTRACT

A mounting system is provided to allow the attachment of an acoustic collector to a handheld electronic device such that sound is conducted directly to the device's microphone. A fitted case or band encloses part of the device and includes a tube running from the collector to the device's microphone. In certain embodiments, the tube may be embedded in the case, and a detachable mount may be provided to connect the collector to the case. The collector may be a stethoscope chestpiece, or an open air collector, such as a parabolic collector.

13 Claims, 9 Drawing Sheets

Related U.S. Application Data continuation of application No. 14/054,656, filed on Oct. 15, 2013, now Pat. No. 9,414,155.

(56) References Cited

U.S. PATENT DOCUMENTS

| | | |
|---|---|---|
| 4,802,550 A | 2/1989 | Poore |
| 4,893,143 A | 1/1990 | Sheng-Huei |
| 5,252,787 A | 10/1993 | Moore et al. |
| 5,357,972 A | 10/1994 | Norlien |
| D353,196 S | 12/1994 | Savage et al. |
| D359,958 S | 7/1995 | Frodelius |
| D394,314 S | 5/1998 | Moore et al. |
| 6,210,344 B1 | 4/2001 | Perin et al. |
| D458,369 S | 6/2002 | Helmholz et al. |
| 6,510,918 B2 | 1/2003 | Bates |
| 6,757,392 B1 | 6/2004 | Granzotto et al. |
| 6,790,178 B1 | 9/2004 | Mault et al. |
| 7,115,102 B2 | 10/2006 | Abbruscato |
| 7,449,650 B2 | 11/2008 | Richardson et al. |
| D591,730 S | 5/2009 | Pantaleone |
| 7,735,598 B2 | 6/2010 | Nakamura |
| 8,170,259 B2 | 5/2012 | Liu et al. |
| 8,200,277 B2 | 6/2012 | Lee |
| D669,587 S | 10/2012 | Mayer |
| 8,287,283 B2 | 10/2012 | Lecat |
| D676,034 S | 2/2013 | Stuart |
| D678,379 S | 3/2013 | O'Neill et al. |
| D678,869 S | 3/2013 | Diebel |
| D679,699 S | 4/2013 | Piedra et al. |
| D680,107 S | 4/2013 | Piedra et al. |
| D685,356 S | 7/2013 | Diebel |
| D685,363 S | 7/2013 | Murchison et al. |
| D686,605 S | 7/2013 | Palmeri |
| D704,183 S | 5/2014 | Guzman |
| 8,759,675 B2 | 6/2014 | Rajeswaran et al. |
| D711,956 S | 8/2014 | Adams |
| 8,863,415 B2 | 10/2014 | Muraco et al. |
| D717,856 S | 11/2014 | Slawson et al. |
| D718,291 S | 11/2014 | Hong |
| D718,760 S | 12/2014 | Davis et al. |
| 8,939,251 B2 | 1/2015 | Ting |
| D723,535 S | 3/2015 | Minn et al. |
| D724,728 S | 3/2015 | Ting |
| D726,704 S | 4/2015 | Park et al. |
| 9,042,568 B2 | 5/2015 | Poplaw |
| D740,267 S | 10/2015 | Diebel |
| D744,472 S | 12/2015 | Lerenthal |
| D744,993 S | 12/2015 | Diebel |
| D746,802 S | 1/2016 | Mulumudi et al. |
| D746,804 S | 1/2016 | Nousiainen |
| 9,243,739 B2 | 1/2016 | Peters |
| D749,554 S | 2/2016 | Park et al. |
| 2001/0030077 A1 | 10/2001 | Watson |
| 2004/0109571 A1 | 6/2004 | Yoshimine |
| 2004/0173401 A1 | 9/2004 | Kurtz |
| 2004/0220487 A1 | 11/2004 | Vyshedskiy et al. |
| 2005/0157887 A1 | 7/2005 | Kim |
| 2008/0146276 A1 | 6/2008 | Lee |
| 2009/0213264 A1 | 8/2009 | Kim |
| 2009/0290725 A1 | 11/2009 | Huang et al. |
| 2010/0023615 A1 | 1/2010 | Grigsby et al. |
| 2010/0232615 A1 | 9/2010 | Sorlander et al. |
| 2011/0064236 A1 | 3/2011 | Schubach |
| 2011/0087135 A1 | 4/2011 | Ferzli et al. |
| 2011/0170725 A1 | 7/2011 | Liu |
| 2012/0027237 A1 | 2/2012 | Lin |
| 2012/0074006 A1 | 3/2012 | Monaco et al. |
| 2012/0190303 A1 | 7/2012 | Wong |
| 2012/0320340 A1 | 12/2012 | Coleman, III |
| 2013/0116584 A1 | 5/2013 | Kapoor |
| 2013/0170686 A1 | 7/2013 | Lester, Jr. |
| 2013/0181584 A1 | 7/2013 | Whitten et al. |
| 2013/0206614 A1 | 8/2013 | O'Neill et al. |
| 2013/0301863 A1 | 11/2013 | Weaver, III |
| 2013/0303000 A1 | 11/2013 | Witter et al. |
| 2014/0005574 A1 | 1/2014 | Ting |
| 2014/0077044 A1 | 3/2014 | Witter et al. |
| 2014/0135080 A1 | 5/2014 | Kimball et al. |
| 2014/0154152 A1 | 6/2014 | Chumanov et al. |
| 2014/0163422 A1 | 6/2014 | Poplaw |
| 2014/0243685 A1 | 8/2014 | Patwardhan et al. |
| 2015/0087926 A1 | 3/2015 | Raz et al. |
| 2015/0094597 A1 | 4/2015 | Mestha et al. |

FOREIGN PATENT DOCUMENTS

| | | |
|---|---|---|
| KR | 20130041559 | 4/2013 |
| WO | WO-2011/049293 A1 | 4/2011 |

OTHER PUBLICATIONS

Canadian Examiner's Report dated Mar. 9, 2017, from application No. 2,927,190.
Canadian Examiner's Report dated Nov. 13, 2015, from application No. 164902.
Canadian Examiner's Report dated Oct. 18, 2014, from application No. 156103.
Canadian Examiner's Report dated Sep. 24, 2015, from application No. 156103.
Chinese Office Action dated Feb. 22, 2017, from application No. 201480064888.3 (No English translation available).
Chinese Office Action dated Sep. 29, 2017, from application No. 201480064888.3 (No English translation available).
European Office Action dated Jan. 2, 2018, from application No. 14853365.6.
Extended European Search Report dated Nov. 17, 2016, from application No. 14853365.6.
International Preliminary Report on Patentability dated Apr. 28, 2016, from application No. PCT/US2014/060493.
International Search Report and Written Opinion dated Jan. 15, 2015, from application No. PCT/US2014/060493.
International Search Report and Written Opinion dated May 23, 2016, from application No. PCT/US2016/017038.
IPhone Stethoscope Attachment by Jeff Thompson http://www.thingiverse.com/thing:149028dated Sep. 25, 2013.
IPhone Stethoscope Attachment Finished as shown in http://www.jeffreythompson.org/blog/2011/12/15/iphone_stethoscope-attachment-finished dated Dec. 15, 2011.
Japanese Office Action dated Jan. 6, 2015, from application No. 2014-008230 (no English translation available).
My Babys Beat http://www.mybabysbeat.com dated Oct. 10, 2013.
Notice of Allowance dated Jul. 31, 2015, from U.S. Appl. No. 29/469,889.
Thinklabs Stethoscope App http://www.thinklabsmedical.com/iphone-a-ipod-touch-app.html dated Oct. 10, 2013.
Thompson, "IPhone Stethoscope Attachment Finished", http://www.jeffreythompson.org/blog/2011/12/15/iphone-stethoscope-attachment-finished/. Dec. 15, 2011.
U.S. Non-Final Office Action dated Jun. 7, 2018, from U.S. Appl. No. 15/857,464.
U.S. Notice of Allowance dated Apr. 4, 2016, from U.S. Appl. No. 14/054,656.
U.S. Notice of Allowance dated Aug. 30, 2017, from U.S. Appl. No. 15/627,313.
U.S. Notice of Allowance dated Dec. 17, 2018, from U.S. Appl. No. 15/857,464.
U.S. Notice of Allowance dated Jan. 29, 2016, from U.S. Appl. No. 29/508,972.
U.S. Notice of Allowance dated Jan. 3, 2017, from U.S. Appl. No. 14/617,807.
U.S. Notice of Allowance dated Jul. 19, 2017, from U.S. Appl. No. 15/627,313.
U.S. Notice of Allowance dated Jun. 29, 2016, from U.S. Appl. No. 29/544,019.
U.S. Notice of Allowance dated Mar. 14, 2017, from U.S. Appl. No. 15/203,680.
U.S. Office Action dated Aug. 12, 2016, from U.S. Appl. No. 14/617,807.

(56) References Cited

OTHER PUBLICATIONS

U.S. Office Action dated Aug. 21, 2015, from U.S. Appl. No. 14/054,656.
U.S. Office Action dated Feb. 9, 2016, from U.S. Appl. No. 14/054,656.
U.S. Office Action dated May 15, 2015, from U.S. Appl. No. 29/469,889.
U.S. Office Action dated Sep. 8, 2016, from U.S. Appl. No. 15/203,680.

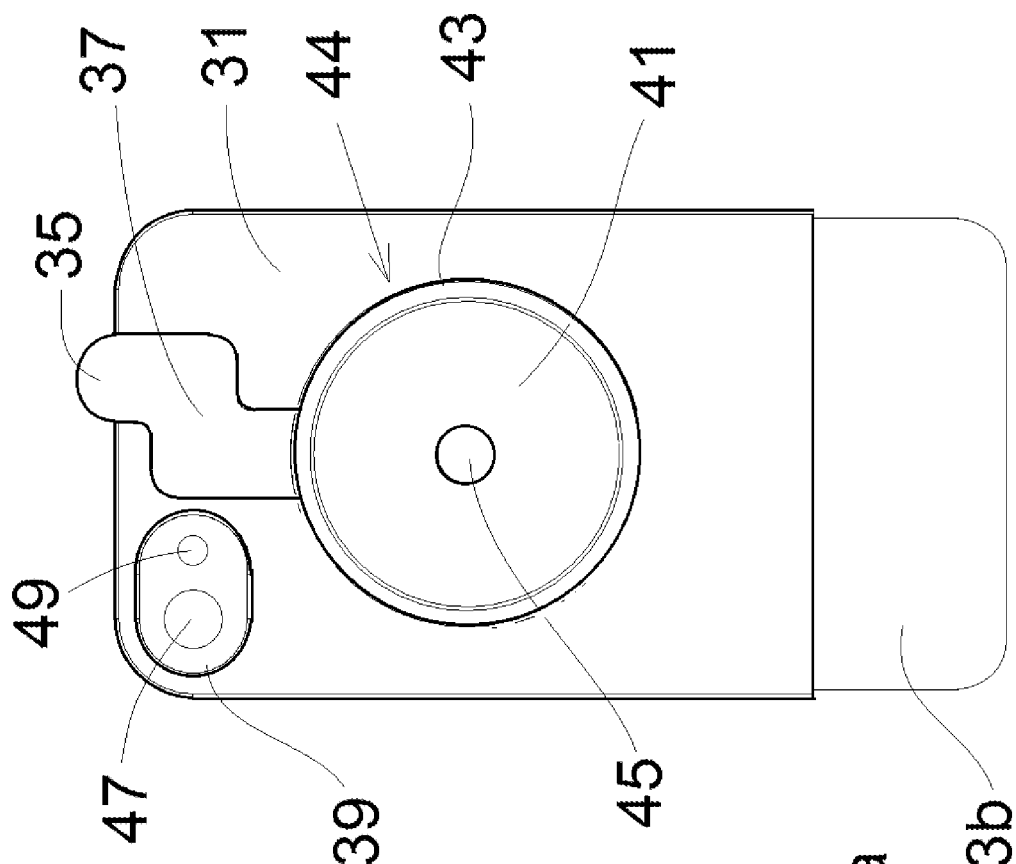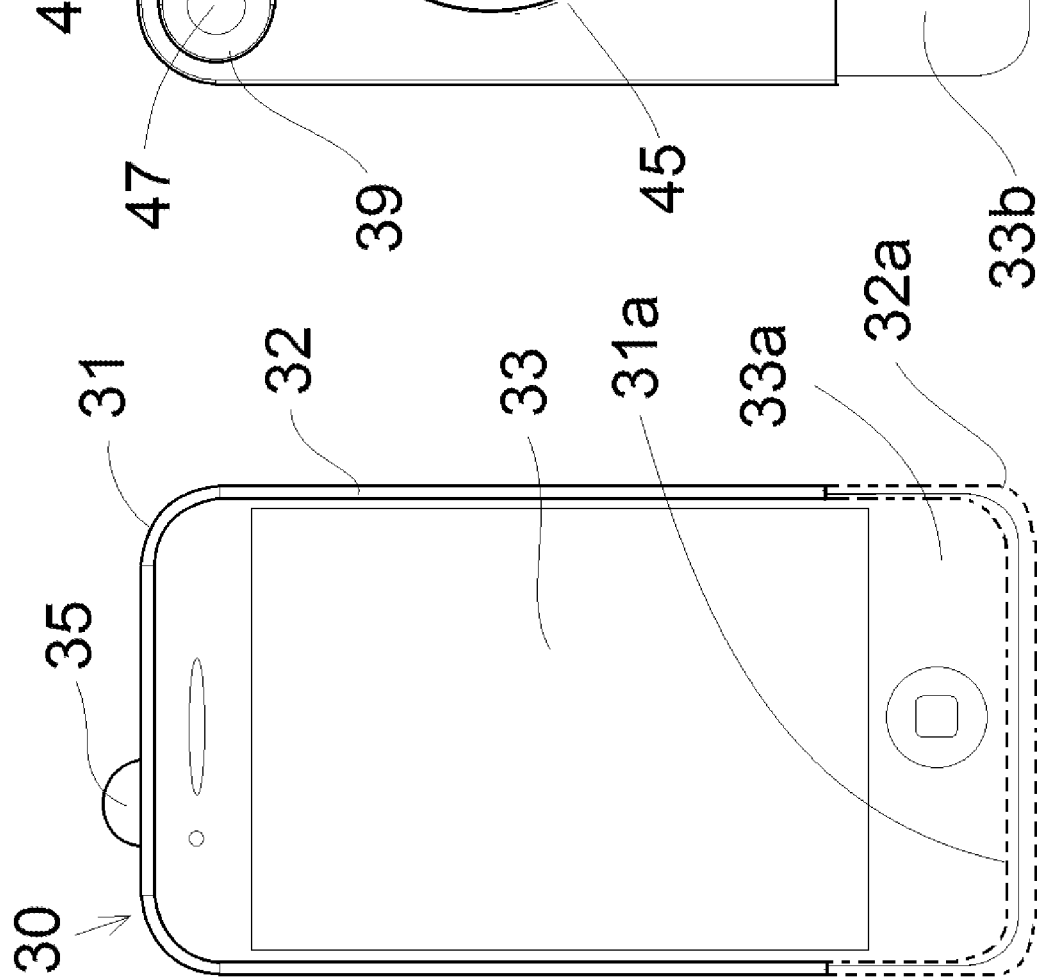

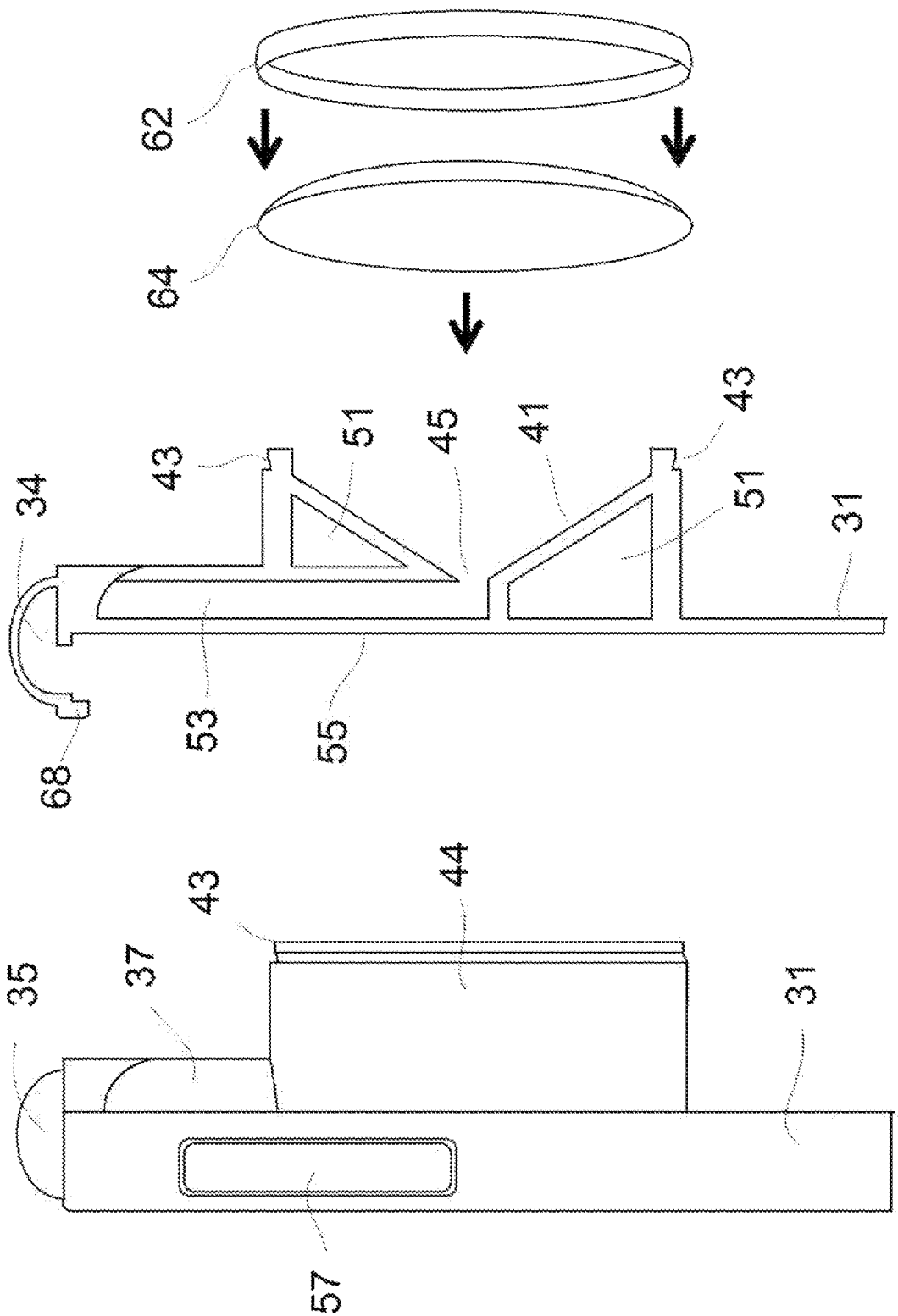

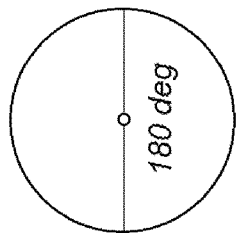
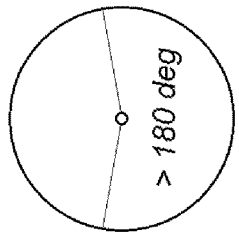
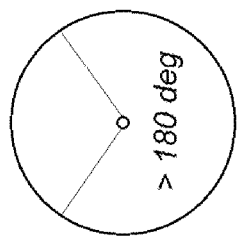
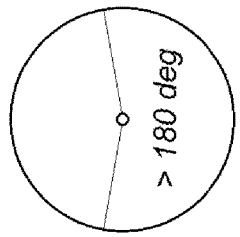
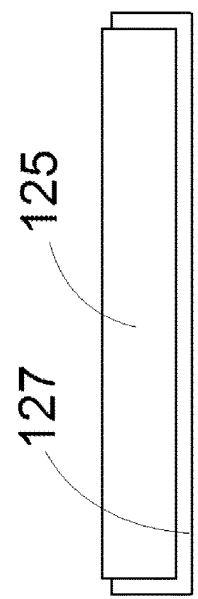
FIG. 2A
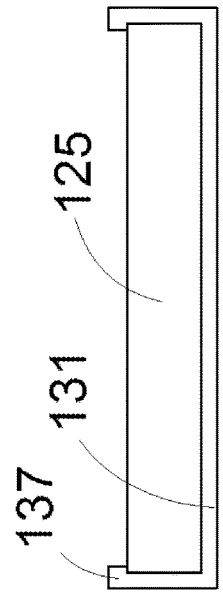
FIG. 2B
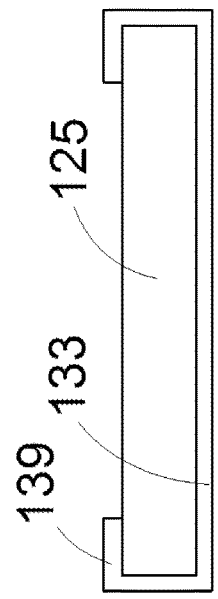
FIG. 2C
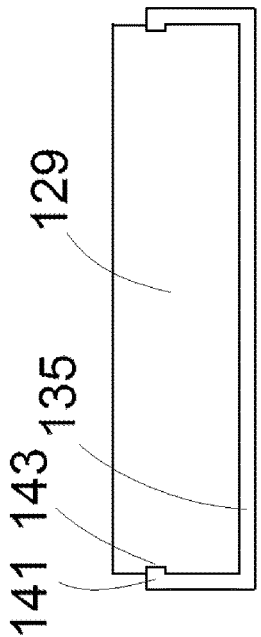
FIG. 2D

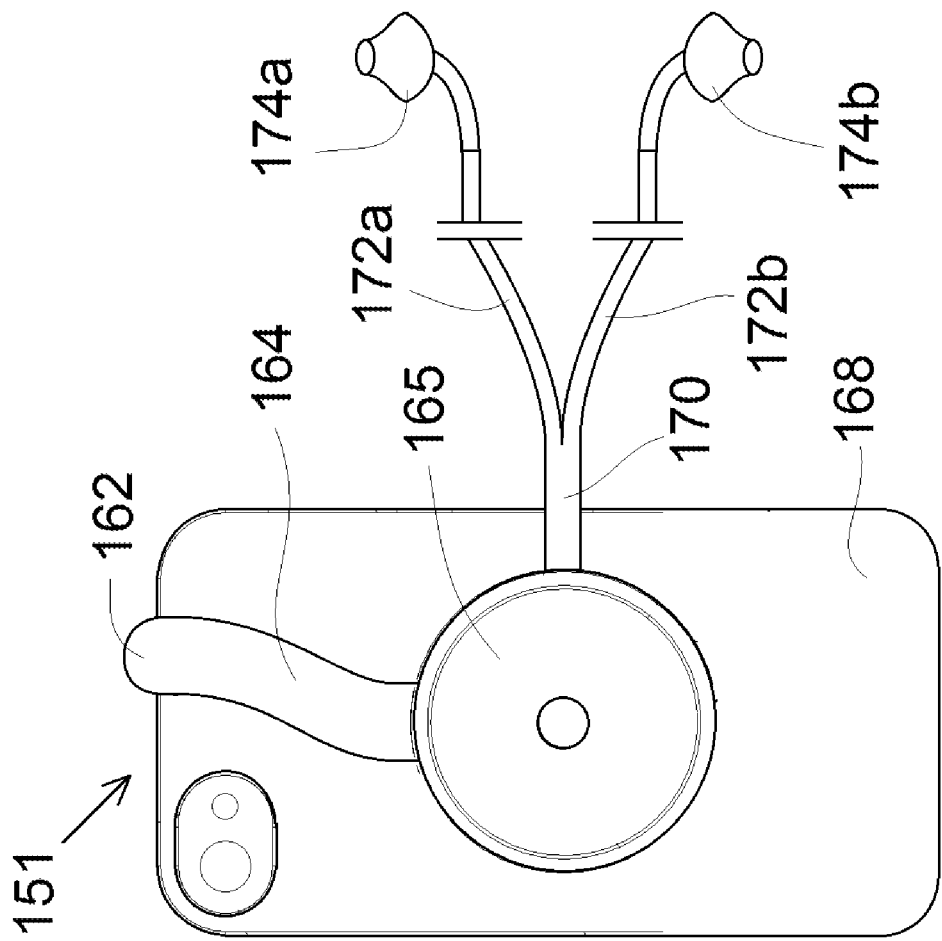
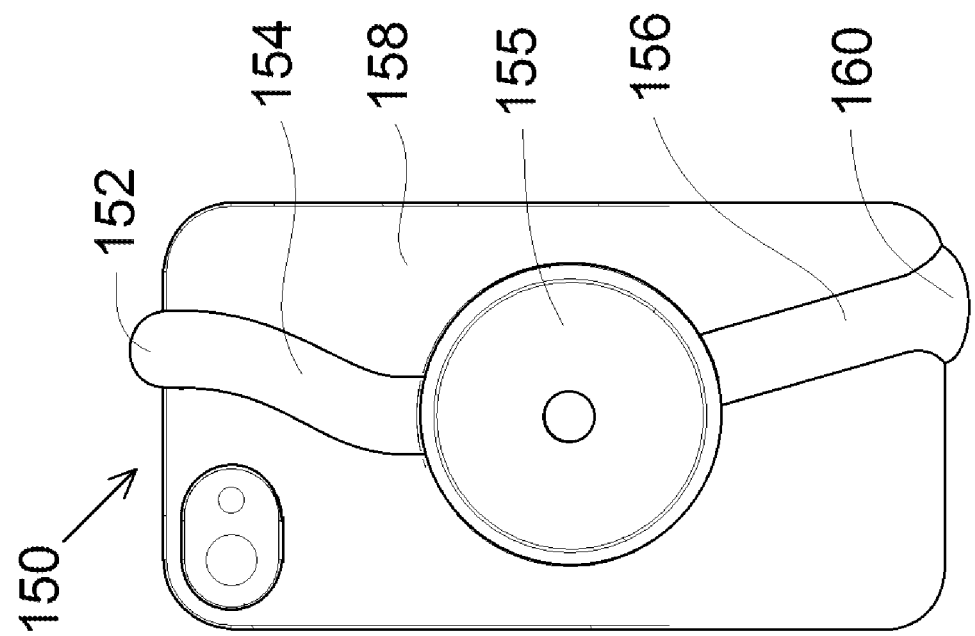

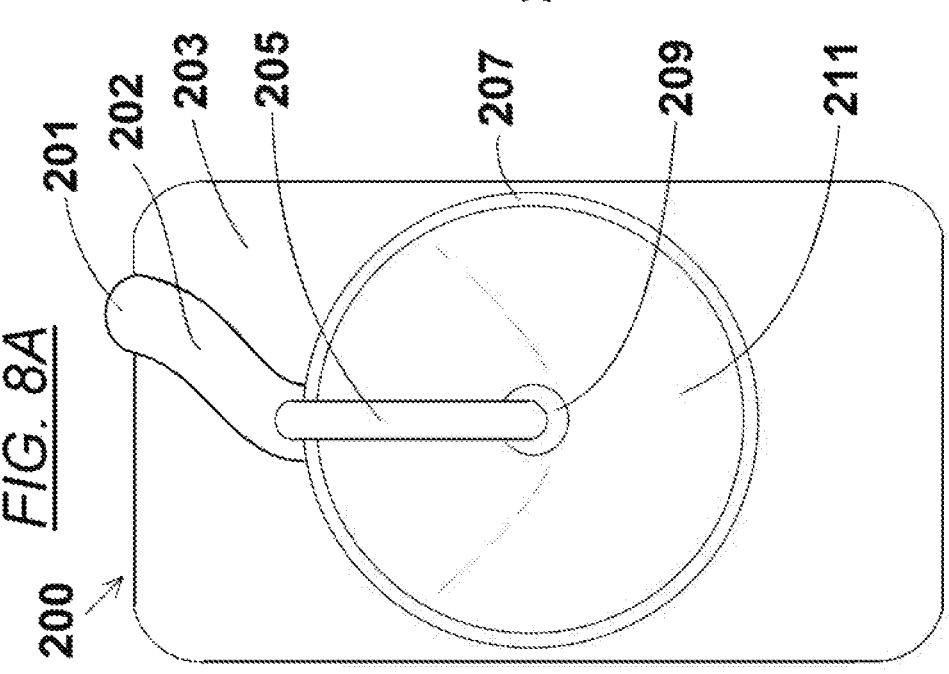

ACOUSTIC COLLECTION SYSTEM FOR HANDHELD ELECTRONIC DEVICES

CROSS-REFERENCE TO RELATED PATENT APPLICATIONS

This application is a Continuation of U.S. patent application Ser. No. 15/857,464, filed Dec. 28, 2017, which is a Continuation of U.S. patent application Ser. No. 15/627,313, filed Jun. 19, 2017, which granted on Jan. 2, 2018 as U.S. Pat. No. 9,855,019, which is a Continuation of U.S. patent application Ser. No. 15/203,680, filed Jul. 6, 2016, which granted on Jul. 18, 2017 as U.S. Pat. No. 9,706,975, which is a Continuation of U.S. patent application Ser. No. 14/054,656, filed Oct. 15, 2013, which granted on Aug. 9, 2016 as U.S. Pat. No. 9,414,155, all of which are incorporated herein by reference in their entirety.

FIELD

The present disclosure relates to the field of acoustic augmentation devices, including stethoscopes and long range sound collectors. The present disclosure also relates to the field of attachment accessories for handheld electronic devices such as smartphones and tablets.

BACKGROUND

Acoustic collection devices comprising funnels, elongated tubes and/or listening bells have been used for centuries. As relevant herein, acoustic collection devices can generally be considered to fall into two categories: (1) stethoscopes for close-range, contact-based sound transmission, and (2) funnels used for contactless, longer range sound detection and amplification, such as parabolic collectors.

The first medical stethoscope is attributed to the nineteenth century French physician Rene Laennec. Stethoscopes have since come to be used ubiquitously not only by doctors, but also by scientists and craftsmen in a broad range of fields that have a need for basic sound conduction/amplification. The modern stethoscope consists of a chestpiece having a hollow stem connected to a length of hollow tubing that leads to two earbuds.

The chestpiece typically consists of two opposite sides, one having a diaphragm that transmits higher frequency sounds, and the other side having a rigid, cupped bell for transmitting lower frequency sounds. The standard stethoscope includes a semi-rigid frame that serves the dual purpose of mounting the ear buds and allowing the stethoscope to hang around the user's neck.

For longer-range, contactless sound collection, funnels are often used. Though no longer in widespread use, ear trumpets were traditionally used to assist people with hearing nearby conversation or sounds. Modernly, parabolic microphones have come into ubiquitous use for gathering sound waves traveling over distances as great as several hundred yards. The design of a parabolic microphone is fairly straightforward: a cone with a parabolic inner wall focuses incoming sound waves at the geometric focal point of the parabola. A microphone is mounted at the focal point to collect the sound. Alternatively, a tube with an opening may be placed at the focal point, and the sound conducted through the tube to a listening location.

In the present disclosure, the generic term "acoustic collector" or "collector" will be used to refer to acoustic collectors in the nature of both (1) stethoscope chestpieces and (2) longer-range, contactless sound collectors, such as funnels and parabolic collectors. These longer-range, contactless acoustic collectors may also be referred to as "open air" collectors because they are not pressed against a surface in the manner of a stethoscope chestpiece. Where the term "stethoscope chestpiece" or "chestpiece" is employed, it should be noted although this disclosure will use those terms to refer to a unit containing a diaphragm and/or a bell, such a unit need not only be used in conjunction with medical evaluations. The "chestpiece" might also be used for any number of applications that benefit from being able to detect sound vibrations through a material. The size and shape of the chestpiece might also vary, along with the type and sensitivity of the diaphragm and/or bell. As used herein, "chestpiece" refers broadly to any unit having a surface for resting against a sound-transmitting material, and a hollow interior for transmitting that sound out through a stem.

With the advent of handheld electronic devices, some have proposed alternative designs for stethoscopes that call for incorporating them with electronic sound recorders and wireless transmitters. For example, it has been proposed to attach a stethoscope chestpiece to an electronic recording device mounted along the tube running to the stethoscope's earbuds. This "in-line" device may be equipped with a microphone and Bluetooth-type transmitter for wirelessly delivering a sound recording.

It has also been proposed that a small stethoscope diaphragm be built into the back of a cellular phone. This design is of limited use, however, because, it would require manufacturing a cellular telephone with a small diaphragm already "embedded" into main body of the phone. This is a specialty-purpose application that most cellular phone manufacturers would not consider. Furthermore, embedding a small diaphragm within the phone limits its size. It has also been proposed to have an electronic wire connection between a stethoscope chestpiece and a jack on the cellular phone, but this is yet another piece of specialty electronic equipment that would require separate manufacture.

Another proposed solution is to physically connect a tube from the chestpiece to the microphone of a cellular phone. Such a design proposes that a phone have a microphone at one end, and that an adapter connects the stethoscope tube directly to the end of the phone equipped with the microphone. These proposals call for the chestpiece to be physically separate from the main body of the electronic device, and in some cases connected only by a long length of tubing. The disadvantages of such proposals include at least: (1) instability of the mounting, (2) difficulty of handling the portable electronic device and the chestpiece as separate items, and (3) poor sound quality and conduction.

Applicants are aware of no proposals for directly mounting a stethoscope chestpiece to a modern portable electronic device such as a smartphone or tablet.

Embodiments that a contactless, open air acoustic collector with a portable electronic device such as portable phones and tablets may be advantageous.

OBJECTS OF THE INVENTION

In light of the foregoing disadvantages of the prior art, it is an object of embodiments of the present invention to provide an acoustic collector mounting system that allows a stethoscope chestpeice or open air collector to be mounted directly to a handheld electronic device as part of a fitted casing.

It is a further object of the invention to allow the mounting of an acoustic collector to modern handheld electronic devices such as smartphones and tablets.

It is a further object of embodiments of the invention to allow for the removable mounting of an acoustic collector directly on a handheld electronic device case.

It is a further object of embodiments of the invention to conveniently allow a variety of stethoscope chestpieces to be mounted to a variety of different handheld electronic devices using a universal attachment mechanism.

It is a further object of embodiments of the invention to allow persons to use a handheld electronic device such as a smartphone to amplify sounds across a room, or a longer distance.

It is a further object of embodiments the invention to provide a means for allowing a user to selectively enhance certain sound frequencies or limit reception to certain sound frequencies.

SUMMARY

The foregoing objectives are achieved by supplying a fitted casing that wraps around at least part of a handheld electronic device. The casing is designed to allow affixing of the acoustic collector to the handheld electronic device, and may include an embedded tube running from one or more of the device's microphones to the collector. The acoustic collector may be a stethoscope chestpiece or a longer-range open air collector, such as a parabolic collector. In certain embodiments, the casing may take the form of a band whose length can be adjusted to fit a variety of electronic devices. In preferred embodiments, the portable electronic device is equipped with software that allows the user to selectively amplify and/or limit certain sound frequencies.

BRIEF DESCRIPTION OF THE DRAWINGS

FIG. 1A is a plan view of an embodiment of the invention.

FIG. 1B is a plan view of the opposite side of the embodiment shown in FIG. 1A.

FIG. 1C is a side external view of the embodiment shown in FIG. 1A.

FIG. 1D is a side cross-sectional view of the embodiment shown in FIG. 1A, also showing other attachable components.

FIGS. 2A-2D are cross-sectional schematic views of casings attached to various devices. The circular diagrams on the right are abstract representations of the extent to which the casings encircle the devices.

FIG. 6A is a plan view of another embodiment of the present invention.

FIG. 6B is a plan view of another embodiment of the present invention.

FIG. 8A is a plan view of another embodiment of the present invention.

FIG. 8B is a side view of the embodiment shown in FIG. 8A.

FIG. 8C is a side cross-sectional view of the embodiment shown in FIG. 8A.

DETAILED DESCRIPTION

Figure 3:
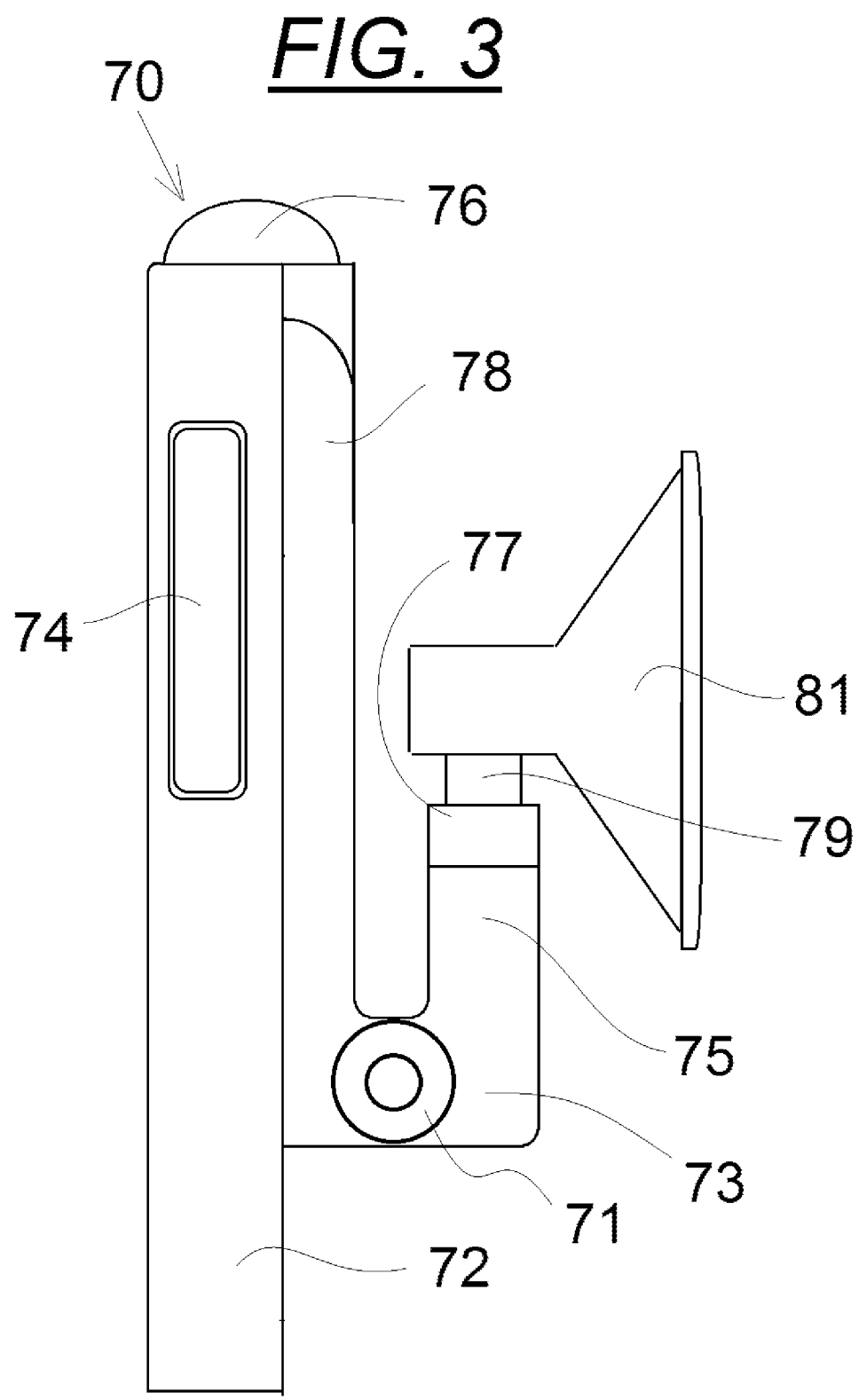
FIG. 3 is a side external view of another embodiment of the present invention.

FIG. 1A depicts an embodiment 30 of the present invention. A sleeve/casing 31 is fit snuggly around a handheld electronic device 33 having front face 32A. The casing 31 is provided with a lip 32 that clasps the edges of device 33, slightly overlapping the front face 32A. The casing 31 may be made of any number of materials, including polymeric material having sufficient rigidity that it will keep lip 32 clasped about the edges of the device 33 during normal use.

As shown, casing 31 only covers the upper portion of device 33. In this mode, casing 31 should have sufficient elastic tension to exert a squeezing force on device 33 to help keep lip 32 engaged and prevent casing 31 from slipping off device 33. In most circumstances, the overlap of lip 32 on the front face 32A need only be barely visible to achieve the desired clasping effect, so long as the casing is sufficiently rigid to keep the rim in place. Adding a rubberized layer or texturing to the surface of casing 31 contacting the device 33 will also improve the casing's its grip.

Alternatively, casing 31 can be designed to wrap more completely around the device as shown by dotted lines representing lower casing portion 31a. Casing portion 31a continues lip 32 as lip 32a, which also clasps the sides of the device 33 and slightly overlaps the front face 32A. When the casing 31 is designed in this manner, it is less likely that device 33 will slip out, and consequently the casing may be made of a more flexible or rubbery material, having sufficient elastic tension that it will keep lips 32 and 32a in overlapping engagement with front face 32A.

The overlapping aspect of the rims just discussed can also be described as the rim "hooking onto" at least a portion of the device such that the casing material wraps around at least a portion of the device by more than 180 degrees, even if the overlap is only slight. This concept is depicted visually in FIGS. 2A-2D. FIG. 2A is a cross-sectional view of a device 125 partially wrapped with a casing 127. The casing 127 does not hook onto the device, and instead only covers three sides that are at right angles to each other. The arc covered by casing 127 is therefore only 180 degrees, which can be understood by thinking of the device 125 in the abstract as the circle shown in the diagram to the right of the figure.

Referring to FIG. 2B, device 125 in encased by casing 131 which has a lip 137 slightly overlapping the front face of the device. In this instance, the arc covered by the casing 131 is slightly greater than 180 degrees. Similarly, in FIG. 2C, the arc covered by casing 133 about device 125 is greater than 180 degree by virtue of lip 139. If the casing completely encircled the device, we would say it covered an arc of 360 degrees.

FIG. 2D depicts an alternative arrangement in which device 129 has an indentation 143 that allows lip 141 of casing 135 to "hook onto" the device 129. The arc covered by casing 135 is therefore slightly greater than 180 degrees.

Generally speaking, "hooking onto" a device will require that the casing cover three faces of the device, and that two opposing edges of the casing have lips that each overlap a fourth surface of the device.

Casings of the kind just described are already made by manufacturers of smartphone accessories, such as Incase Designs Corporation, and their construction is known in the art. To the applicant's knowledge, however, no handheld electronic device casing manufacturer has yet proposed incorporating a stethoscope chestpiece with such a casing.

Returning now to FIG. 1A, the microphone end 35 of hollow tube 37 (shown in FIG. 1B) is visible at the top of device 33. The location of the microphone end 35 is dictated by the location of the recording microphone on the device. In many modern smartphones and tablets, there may be more than one microphone on the device. In the case of the iPhone 4S, for example, there are two microphones present. A first microphone has an aperture located off-center on the top of the device. A second microphone (which is used for picking up voice during normal telephone operation) is located off-center at the bottom of the device. Either microphone could be used for the invention, but the top microphone is preferred because it enables the user to audibly interact with the device (i.e. phone call, digital voice assistant, voice recording, etc.) without removing the casing from the device.

Referring now to FIG. 1B, the other side of embodiment 30 is depicted. An opening 39 in casing 31 exposes the camera aperture 47 and flash element 49 of device 33, shown here with its rear face 32B partially exposed. It may be advantageous to combine audio recordings made with the acoustic collector with visual recordings (still images or video) made by the camera. For example, if the invention is used as a medical stethoscope, the audio recordings may be combined in the same computer file with pictures or video of the patient taken which the audio recordings were being made. In another example, if the invention is used as on open air collector to detect sound across a long distance during a live event (such as a sporting event), the camera can be used to simultaneously record video of event.

The microphone end 35 of hollow tube 37—and hollow tube 37 itself—are incorporated with casing 31, and can be cast in the same mold, or printed by the same 3D printer. Hollow tube 37 curves and runs along the back of casing 31 toward the center of the casing.

FIG. 1B shows embodiment 30 provided with an embedded acoustic collector 44, which, like the hollow tube 37, can be cast in the same mold as casing 31, or printed on the same 3D printer. When the collector is cast from the same mold as the casing, or printed on the same 3D printer, or otherwise manufactured as permanently affixed to the casing, the collector will be referred to as "incorporated with the casing."

As a general matter, any funnel-like structure can serve as an acoustic collector for both stethoscope and longer-range sound collection purposes. As will be described, the collector 44 shown here is specially configured to be used as a stethoscope chestpiece, though could also be used for longer-range sound collection. FIGS. 8A-8C, by comparison, depict an alternative embodiment in which the collector is specifically intended for long-range, open air sound collection.

Returning to FIG. 1B, the hollow tube 37 runs along the back of casing 31 and opens at hole 45 of embedded collector 44. The embedded collector 44 has a sloped inner wall 41 that extends outward from hole 45. Embedded collector 44 is provided with a grooved or threaded outer rim 43 for mounting a diaphragm or other circular attachments, such as a rubberized O-ring. As such, collector 44 is specially designed to be used as a stethoscope chestpiece (though could also be used for longer-range open air sound collection).

When designed to mount a diaphragm, collector 44 is preferably constructed of a rigid material such as hard plastic or metal. However, when used on its own as a stethoscope chestpiece without a diaphragm, it will be advantageous to construct the collector 44 from a flexible rubber material that can deform to match the contours of the surface being listened to such that it forms a good seal. Alternatively, the lip 43 can be fitted with a flexible rubber sealing ring to accomplish the same purpose, as discussed further below.

FIG. 1C is a side view of the exterior of embodiment 30, shown here on its own without the device 33. An opening 57 is provided for buttons along the side of device 33. Similar openings may be placed wherever necessary to access the surface of the device 33. Hollow tube 37 is shown running along the back surface of casing 31, with embedded collector 44 protruding outward.

FIG. 1D is a cross-sectional view of embodiment 30. The inner backing 55 of casing 31 would be substantially flush against the back of the device 33 when the casing is attached to the device. Similarly, upper lip 68 of lip 32 would partially overlap the front face 32A of the device 33, thereby hooking onto the device in conjunction with the side portions of lip 32. Hollow tube 37 is shown as having a hollow core 53 that runs from collector hole 45 to the microphone end opening 34.

The embedded collector 44 may be constructed with a hollow chamber 51 behind sloped inner wall 41. This design will decrease the quantity of material in (and therefore the weight of) the casing. Hollow chamber 51 can be filled with materials having certain sound dampening/transmission properties to suit the particular application of the stethoscope chestpiece.

FIG. 1D depicts embedded collector 44 with a grooved rim 43. This rim can serve multiple purposes. In one mode, it can be designed as the attachment point for a rigid circular collar 62 that mounts diaphragm 64. Screw threading can be added to rim 43 for mounting collars with corresponding threading. Alternatively, a collar may be provided capable of snap-fitting over rim 43. Rim 43 can also serve as the mounting point for an elastic O-ring, also used for attachment of a diaphragm.

As a practical matter, many modern stethoscope chestpiece diaphragms are about 1.7 inches in diameter. For example, the ubiquitous Littmann brand stethoscopes (manufactured by 3M), traditionally have chestpieces with diameters of about 1.7 inches. It will thus be advantageous to design collector 44 to accommodate diaphragms having that dimension (assuming it is intended to be used as a stethoscope chestpiece).

Depending on the use the collector is being put to, collector 44 need not be fitted with a diaphragm. For example, collector 44 can be used as a bell for detecting lower frequency sounds. Its use as a bell will be improved by fitting rim 43 with a rubberized ring for creating a seal over the listening surface. As noted, collector 44 can also be used as a longer-range sound collector. For example, a hearing impaired person might use collector 44 to collect and amplify sound across a room. An attendee at a live performance or sporting event might also use collector 44 to amplify sound over a longer distance.

Although the invention has thus far been shown with the collector located on the broad surface of the casing, the casing may also be designed with the collector located in any of a variety of other positions. For instance, the collector may be attached to the edge of the case, acoustically coupled directly with the device's microphone. The size of the collector may vary depending on the size of the device it is being coupled with. If the collector is attached to the edge of the device, the size of the attachment will be in congruence with the size of the device's edge.

It should also be noted that in the above-described embodiment, and in the embodiments that follow, it will be advantageous to design the opening of the hollow tube over the microphone to have a rubberized or gel sealing ring that can be compressed by the casing to form a tight seal between the tube and the microphone. This added seal will help improve audio transmission quality.

It should additionally be noted that the invention can operate with the acoustic collector physically separate and independently moveable from the casing, with a length of flexible tubing connecting the collector to the handheld device's microphone. This is in contrast to the embodiments depicted in the Figures, which show the collector affixed to the casing, either because it is directly bonded (i.e., incorporated with) with the casing, or detachably mounted in such a way that any independent movement is substantially restricted. For example, the collector 81 of embodiment 70 in FIG. 3 is still deemed "affixed" to the casing 72 because the neck 73 can be made rigid with respect to the casing 72 such that the collector 81 does not move freely from the casing 72.

While the figures herein depict tubing as embedded within the casing, the tubing could just as easily be fixed to the outside of the casing. As a practical matter it may be easier to manufacture the casing with the tubing as an embedded channel, which also reduces the extent to which the tube projects out from the side of the casing. Whether embedded or attached to the outside of the casing, such rigidly fixed tubing may be referred to herein is as "fixed" to the casing (as opposed to extending away from the casing as an independent component).

FIG. 3 depicts an alternative embodiment 70 of the invention designed to allow easy mounting of a collector having a stem. Because many stethoscope chestpieces have stems, embodiment 70 is particularly suited to use with such chestpieces, though it could also be used with an open air collector having a stem (or, as discussed below, with any collector that can be attached to the device by other means).

Here, a casing 72 is provided much like casing 31. Just as in embodiment 30, a hollow tube 78 is incorporated with the casing, and runs to a microphone end 76 opening over the recording microphone aperture of the handheld electronic device. Here, however, the hollow tube 78 bends around juncture 73 and curves outward and upward to form neck 75.

The juncture 73 and neck 75 may be made of a relatively stiff material, such as rigid polymeric material or the like, such that it will tend to hold the chestpiece securely. The chestpiece is thereby prevented from pivoting relative to the casing. Alternatively, the juncture 73 may be provided with a pivot joint 71 that allows the neck 75 to pivot relative to the casing 72. The joint could be designed to have sufficient friction that it will tend to remain in a given position unless moved by the user. Alternatively, the joint 71 could be provided with a screw that can be loosed to pivot neck 75 and then tightened to hold it in place.

In an alternative embodiment (not shown) the collector might be directly attached to the casing by a pivot joint such as a ball and socket joint that allows the collector to pivot relative to the casing. In such an embodiment, each of the ball and socket would have a hole to allow the transmission of sound to the tubing that runs to the electronic device's microphone. The hole openings in the ball and the socket would have to be wide enough such that an air passage can be maintained between the ball and socket even if the collector is pivoted.

As shown in the particular embodiment depicted in FIG. 3, neck 75 is designed to be wide enough to accommodate most stethoscope chestpiece stems, which typically are less than a half inch in diameter. The design would of course work with an open air collector having a similar stem diameter, or the neck 75 could be designed to have whatever diameter is called for by the user's application. A rubberized mating washer 77 may be provided to improve the seal and grip around stem 79 of collector 81. The washer 77 may be made of a rubberized material with a relatively narrow opening capable of elastically expanding to accommodate and securely grip stem 79. Alternatively, removable washers of various sizes may be provided with the device for mounting collectors with stems having different diameters. Embodiment 70 thus enables users to supply their own collector, and modify the mounting system to conform to the user's selection.

Having a neck-and-stem system has the added advantage of allowing the collector 81 to rotate within the neck 75 to whatever angle is desired by the user. Alternatively, embodiment 70 could be designed with the collector permanently incorporated with the neck, and if rotational pivoting is desired, a rotary joint could be added to neck 75. As with pivot joint 71, the rotary joint could be designed to have sufficient friction that it will tend to stay in a given position unless moved by the user.

Figure 4B:
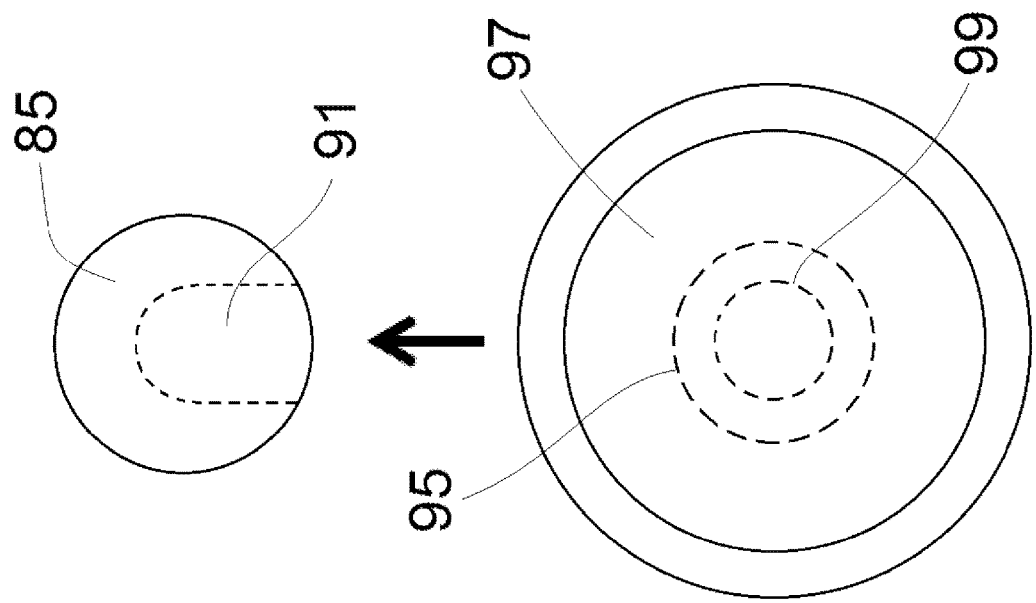
FIG. 4B is a plan view of the portion of the embodiment shown in FIG. 4A.
Figure 4A:
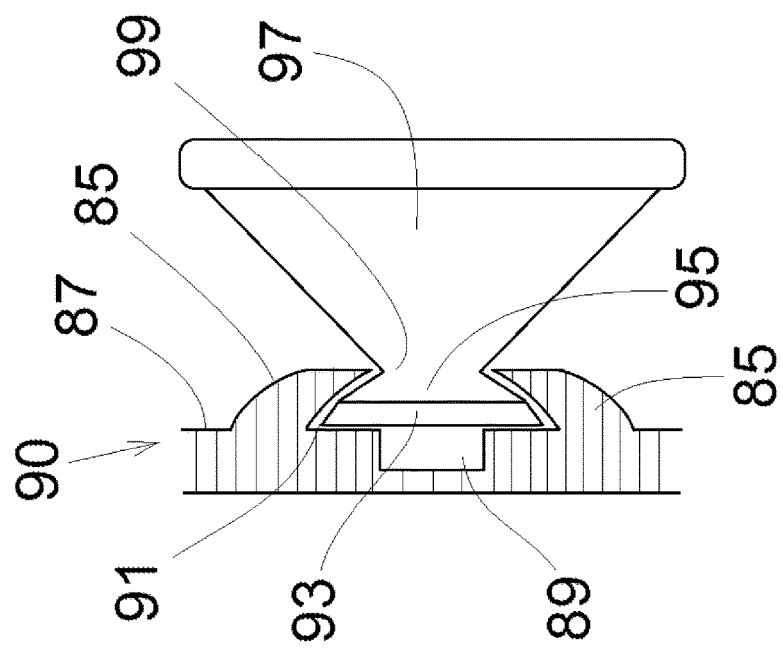
FIG. 4A is a side view of a portion of an embodiment of the present invention, including a partial cross-sectional view indicated by stripes.

FIG. 4A is a side view of a system 90 for directly mounting a collector to a casing 87. Here, the casing (shown in cross-section) is provided with an embedded hollow tube with hollow core 89, like hollow core 53. A raised slot 85 is provided on the surface of casing 87 for mounting the pinched end 95 of collector 97. The opening of slot 85 is just wide enough to accommodate the pinched neck 99 of collector 97. The pinched end 95 of collector 97 fills a correspondingly shaped cavity 91 within slot 85. End 95 is provided with a rubberized tip 93 to form a seal with the inner walls of cavity 91 about the hollow core opening 89.

FIG. 4B is a plan view of the mounting system 90. Raised slot 85 is shown with dotted lines indicating inner cavity 91. Collector 97 is shown with dotted lines representing pinched neck 99 and pinched end 95 on the opposite side of the collector facing casing 87. The user can mount the collector 97 to the casing 87 by sliding the pinched end 95 into the cavity 91 of slot 85. Rubberized tip 93 can be made slightly larger than the cavity space so that it will elastically compress and form a tight seal that will help conduct sound and prevent the collector from disconnecting from the casing.

Figure 5:
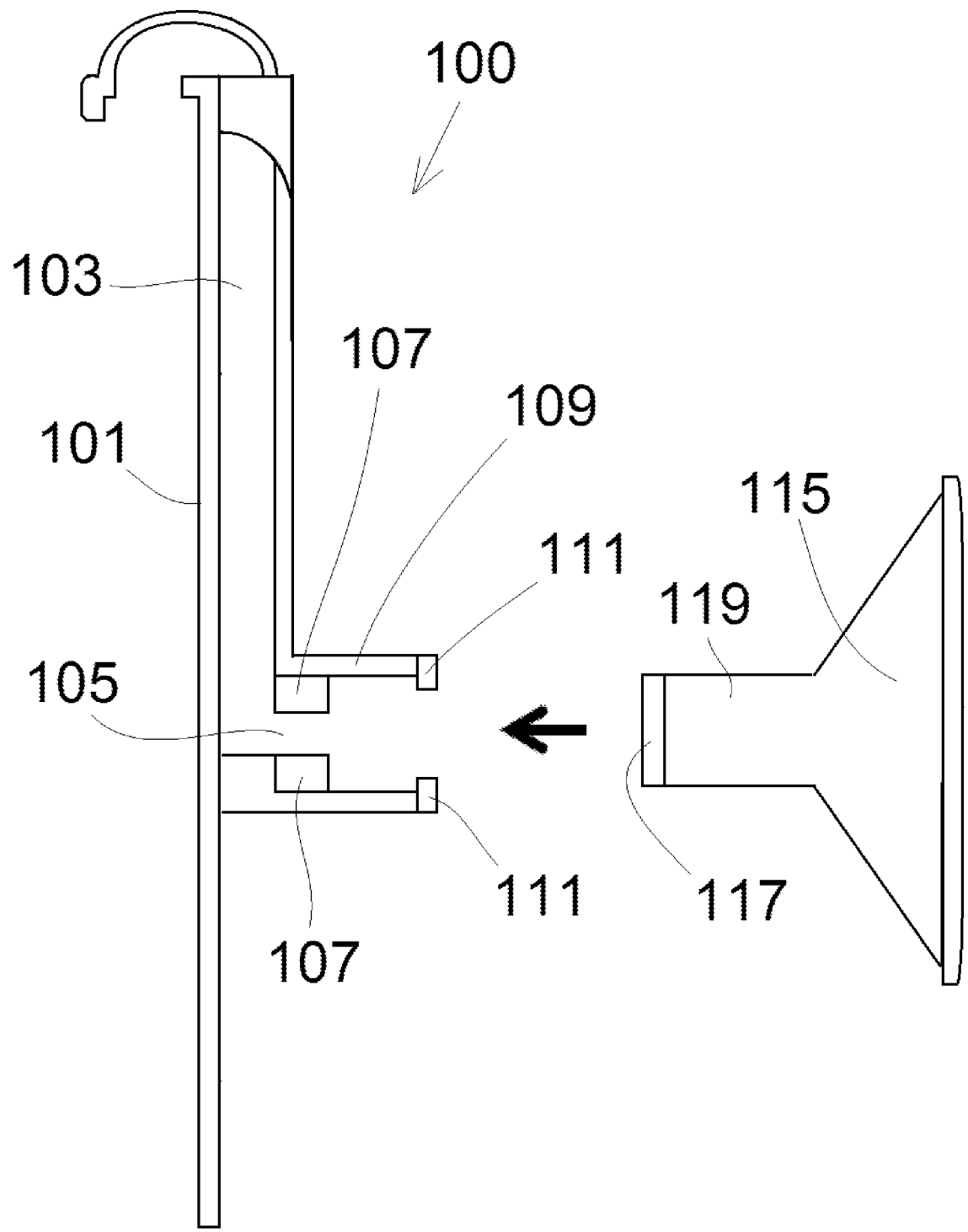
FIG. 5 is a side cross-sectional view of an embodiment of the present invention.

FIG. 5 depicts another embodiment 100 of the present invention featuring an alternative mounting system. Here, a casing 101 (shown in cross-section) is provided similar to casing 31. A hollow tube with hollow core 103 runs to an opening 105 on the back of the casing 101. Here, a substantially rigid neck 109 is provided for mounting a corresponding stem 119 of collector 115. A rubberized ring 111 encircles the tip of neck 109 and provides a tight seal for stem 119.

Neck 109 may also be provided with magnetic portions 107 for attaching to a corresponding magnet or ferromagnetic material 117 at the tip of stem 119. If magnets are used, they should be selected to have a level of intensity such that, depending on their location relative to the handheld electronic device and the type of electronic device used, the magnets will not interfere with the function of the electronic device. The selection of magnets will thus depend on the technical parameters of the handheld electronic device being used with embodiment 100.

FIG. 6A depicts an alternative embodiment 150 of the invention. Here, the casing 158 has been designed to cover the entire backing of the handheld electronic device (rather than just the upper portion as in previous embodiments). In this regard, the casing 158 is much like standard protective casings currently sold by companies such as Incase as accessories to smartphones.

The hollow tube 154 is embedded along an angle in the casing 158 (rather than with 90 degree joints as previously shown). It should be noted that although the invention can be used with angled tubing such as that shown in previous figures, it is preferred to have tubing that runs along the shortest distance with the fewest bends. The shorter the tubing and the fewer bends it has, the better the sound transmission.

Also included in embodiment 150 is a second tubing 156 branching off of the collector 155. This second tubing 156 terminates in an open end 160 that covers a second microphone on the opposite side if the device. In this manner, the device 150 is capable of delivering sound to two different microphones, even if only one is used at a time.

FIG. 6B depicts an alternative embodiment 151 of the invention which has a first tube 164 running to the handheld device's microphone, as well as a second branching tube 170 that extends beyond the casing 168 and splits into ear channels 172a and 172b. These ear channels function like those of conventional stethoscopes and terminate in ear buds 174a and 174b. Note that the full length of ear channels 172a and 172b has been truncated here for illustrative purposes. Embodiment 151 allows the user to listen to the stethoscope at the same time as the handheld device's microphone registers the sounds it conducts.

It should be noted that the branching second tube 170 could just as easily be connected to a different form of listening device, such as a second microphone. This second microphone could also in turn be paired with a recording device or speaker that is physically separate from the main handheld device.

Figure 7B:
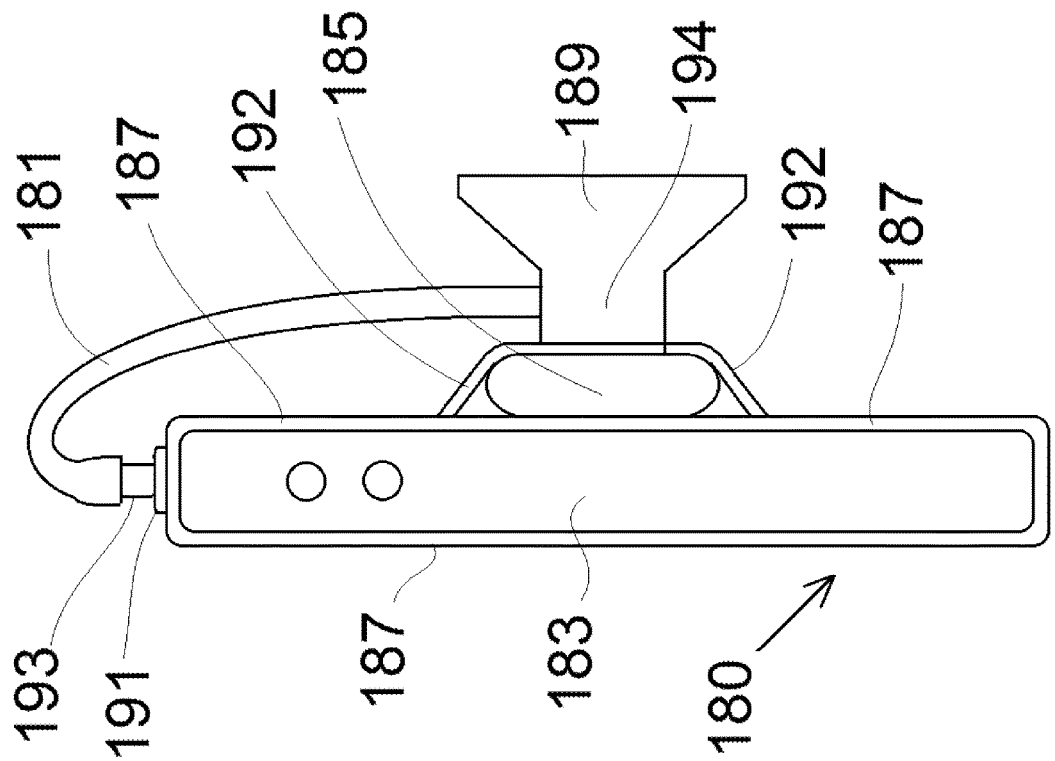
FIG. 7B is a side view of the embodiment shown in FIG. 7A.
Figure 7A:
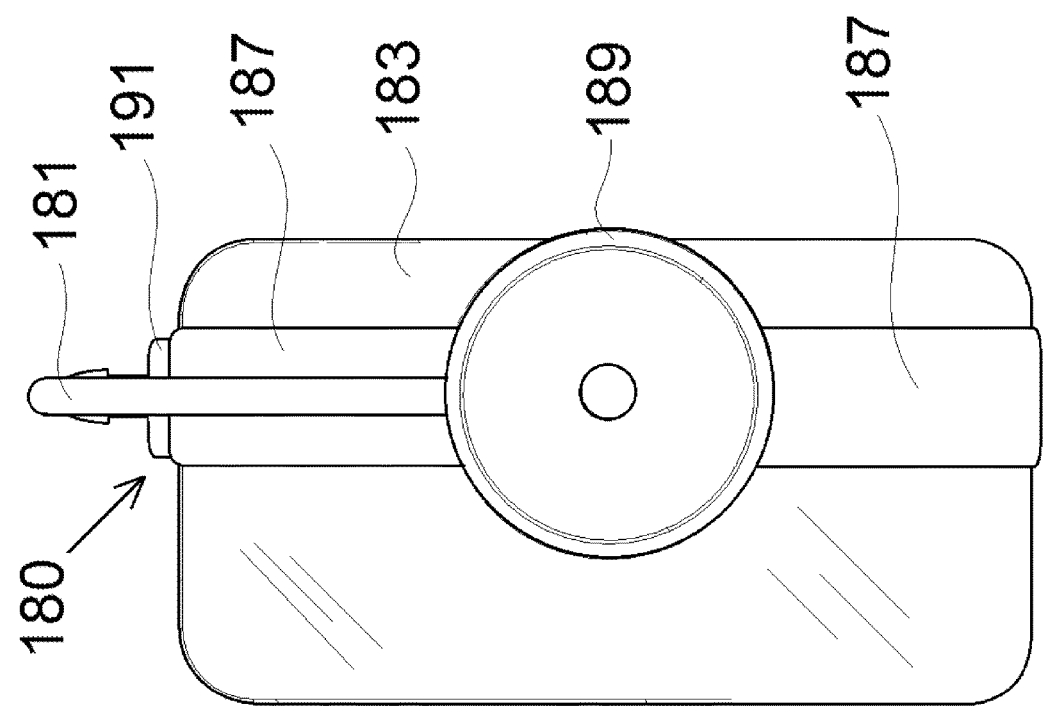
FIG. 7A is a plan view of another embodiment of the present invention.

FIGS. 7A and 7B show yet another alternative embodiment 180 of the invention that eliminates the casing and replaces it with a band 187 that encircles the handheld electronic device 183. Band 187 is preferably elastic and sized to tightly wrap around the device 183. Alternatively, band 187 may be equipped with a commonplace length adjuster—such as a notched belt buckle, or Velcro ends (not shown)—that allow the user to wrap it around device 183 with a desired tightness.

Included with belt 187 is a microphone mounting port 193 that allows attachment of a hollow collector tube 181. The port 193 is preferably made of rigid hollow plastic, and the tube 181 is preferably made of a rubber-like material having sufficient elasticity to mate with port 193 as shown in FIG. 7B. A port base 191—included with the belt 187—has a rubber seal for forming an sealed connection with the microphone on device 183.

Rather than employing a mounting port 193, the port might alternatively feature a magnetic ring, and the corresponding end of tube 181 provided with a mating magnetic ring. Thus, the paired ring magnets would hold the end of tube 181 directly over the microphone port by the force of magnetic attraction.

A collector may be incorporated directly into belt 187, with tube 181 running from the collector to the port 193. When it is desired to use the invention as a stethoscope, the device 180 can also take advantage of the fact that many chestpieces have bulbous ends, and use one or the other of those bulbous ends to secure the chestpiece to the belt 187. FIG. 7B shows a chestpiece 189 having a bulbous bell 185. Belt 187 is equipped with a fitting 192 for grabbing bell 185 and holding it fixed against belt 187. Additional padding may be added to the portion of belt 187 that contacts the chestpiece to reduce sound conduction directly into the device 183.

The fitting 192 is preferably an elastic band with a hole having a diameter similar to the diameter of the central portion 194 of chestpiece 189. The user can stretch open the elastic hole of fitting 192 to accommodate bell 185. In this case, the length of fitting 192 should be such that it elastically holds bell 185 tightly to belt 187.

Embodiment 180 thus advantageously allows the user to employ the invention with a wide range of stethoscope chestpieces and tubing of the user's selection, and does not require selling the chestpiece with the device.

FIGS. 8A-8C depict an alternative embodiment 200 of the invention specially designed to be used as a contactless, longer-range sound collector, i.e., and "open air" collector. FIG. 8A depicts a handheld electronic device casing 203 (in this case, similar to a standard iPhone casing). Directly attached to that casing is a parabolic sound collector dish 207 which has a parabolically sloped inner wall 211. A rigid focal point tube 205 extends across the valley created by the parabolically sloped inner wall 211 and opens to funnel 209 located at the geometric focal point of the parabola. The geometric focal point is the location at which the collector dish 207 will concentrate sound waves. Focal point tube 205 connects with embedded casing tube 202, which terminates at microphone end 201 over the device's microphone.

FIG. 8B is a side view of embodiment 200 showing how the focal point tube 205 traverses the opening of collector dish 207. FIG. 8C is a cross-sectional view of FIG. 8B that shows the parabolic curve of inner wall 211. Focal point tube 205 opens at funnel opening 209a of funnel end 209. Funnel 209 collects the sound that is reflected to the focal point of parabolic inner wall 207. Those sound waves are then transmitted through the tubing channel 215 to microphone end 201. Lips 213 and 217 of casing 203 hook onto the handheld electronic device (not shown), and keep the embodiment 200 securely attached to it.

Though not shown in the drawings, it is also possible for the collector dish and focal point tubing to be a separate unit capable of moving independently from the handheld electronic device and connected to the handheld electronic device via a length of flexible tubing. Such an embodiment would allow larger collector dishes to be used as they could be supported by the user's hand rather relying solely on the support of the casing.

A test was performed using a device casing and collector similar to that shown in FIGS. 1A-1D. First, an iPhone (model 4S) was placed at approximately 14 feet from a constant sound source. A comparison was made between the sound registered by the iPhone without the invention attached and with the invention attached. When the invention was attached, a marked increase in volume was observed.

Varieties of Handheld Electronic Devices

While the drawings herein depict a casing used with an electronic device similar to an early model iPhone, it should be understood that the present invention can be used with a wide variety of handheld electronic devices such as tablets, smartphones, cellular phones and the like. The invention might also be used with any number of other handheld electronic devices of any shape by using the same lips and attachment means disclosed herein.

As used herein, "handheld electronic device" specifically includes (but is not limited to) iPhones (and similar devices), iPads (and similar devices), tablets, smartphones, iPods equipped with microphones (and similar devices), and mobile telephones. "Smartphone" refers to any wireless phone having a generally flat, rectangular shape, such as an Apple iPhone or Samsung Galaxy phone (as well as any similar-functioning, flat handheld devices that may yet come to market not having a rectangular shape). "Tablet" refers to any microphone-equipped handheld electronic device that has a generally flat, rectangular shape, but which may not be equipped with a telephone feature (as well as any similar-functioning, flat handheld devices that may yet come to market not having a rectangular shape). Tablets include, for example, the Apple iPad, the Barnes & Noble Nook, and the Microsoft Surface. The term "Smartphone/Tablet" encompasses both of those terms as just defined.

According to the present invention, an acoustic collector may be mounted to such handheld electronic devices by providing a fitted casing that is capable of wrapping around at least a portion of the device and hooking onto it (as discussed above), with a hollow audio tube connected to the casing and positioned over the device's microphone.

It is also possible that a casing could be made to attach to a handheld electronic device without hooking onto it as shown in FIGS. 2B-2D. For example, the embodiments shown in FIGS. 1A-1D could be functional without lip 32. One way this could be accomplished is by using a magnetic attachment means to hold the casing to the electronic device. For example, small magnets could be embedded within the edges of the casing that tend to attract the corresponding edges of the electronic device. Or a magnet could be embedded with the broad portion f the casing. Wherever magnets are used throughout this disclosure, care should be taken to investigate whether the particular electronic device being used might be disrupted by magnetic fields in certain locations. Devices such as the iPad are known to employ magnets along their edges without disruption of the functioning of the device. Alternatively, if it is desired not to use either lips or magnets, the user could simply "pinch" the casing to the electronic device while it is in use to ensure that the casing does not become dislodged.

It should be noted that it is advantageous to be able to use the present invention with a speaker so that the user can listen to the sounds conducted through the stethoscope at the same time as those sounds are being received by the electronic device's microphone. Most Smartphone/Tablets include their own speakers that can provide such simultaneous sound projection. Feedback effects can be minimized by ensuring a tight seal around the microphone. Additionally, software applications are available that reduce microphone feedback.

Alternatively, as shown in FIG. 6B, a secondary tubing can branch from the device and be connected to a separate listening instrument. That instrument can be a separate microphone and speaker system for projecting the sounds conducted by the stethoscope. Providing a separate speaker unit of this kind will allow the sounds to be projected in a separate location, and will minimize feedback effects.

Applicants note that Smartphone/Tablet devices may yet come to market that are made of thin, flexible material, allowing them to bend or even roll up like paper. It has already been proposed to introduce such products using OLED technology. The present invention can be adapted to work with such thin, flexible devices by providing a rigid or semi-rigid casing that covers most or all of the device, and which has one or more padded lips that can be tightened about an edge (or edges) of the flexible device. For example, a clipboard-type clamping mechanism can be incorporated into the casing lip to clamp an edge of the flexible device. Alternatively, the casing could be designed with edge lips that hook onto opposite sides of the flexible device, and a chord could be extended from opposite sides of the casing across the face of the device to hold it into the casing. Rather than using lips, the casing might include one or more suction cups for attachment to the flexible device. To the extent the flexible device has a metallic component, magnets could also be used to affix the device to the casing.

Alternatively, a casing could be provided with a central slot, allowing all or part of the flexible Smartphone/Tablet device to slide into the casing and be held rigidly therein, in much the same manner as a hardcopy photograph may be slid into a slotted picture frame. Such a casing could have a partially open face to allow access to the viewing screen of the flexible device. The casing might also be constructed of a clear plastic material to allow the user to see through the casing to the viewing screen of the device. Where a casing with a slot is used, the sound transmission tubing could be embedded in a predetermined location within the casing such that it opens over the flexible device's microphone when the flexible device is inserted into the slot.

Frequency Manipulation Software

A problem that arises when using a sound collector is that often many more frequencies of sounds are collected than the user actually wishes to hear. Furthermore, the frequencies that are of interest to the user may have less strength than others (and therefore may not be loud enough). In the context of the present invention, this problem can be conveniently solved by providing the handheld electronic device in question with a software program that is capable of eliminating unwanted sound frequencies and/or amplifying desired sound frequencies.

As an example, human heart sounds typically fall in a range less than about 150 hz. A test was performed recording a human heart sound using a stethoscope connected by a tube to an iPhone microphone. The recorded heart sounds turned out to be of sub-par quality. Then, commercially available audio frequency manipulation software applications were employed in conjunction with an embodiment of the invention similar to that shown in FIGS. 1A-1D. These software programs included the Thinklabs Stethoscope Application and an application entitled "My Baby's Beat" (an application intended to allow pregnant mothers to record their baby's heart sounds). By using this audio frequency manipulation software in conjunction with the invention, a much clearer sound output was achieved. Although many sound frequency augmentation, equalization and/or elimination software programs exist on the market and are known to those of skill in the art of digital sound manipulation, applicants are not aware of anyone proposing the use of such programs in conjunction with an acoustic collector mounted to a handheld electronic device, as proposed herein.

In a preferred embodiment, the present invention will be accompanied by a sound frequency manipulation software installed on the handheld electronic device and capable of amplifying certain frequencies and/or limiting or eliminating others. Because most users will not be familiar with the frequency range of the sounds they desire to listen to, it will be advantageous for the program to provide a simple visual frequency range selector tool so the user can actively vary which frequencies are augmented to identify the best possible sound output. Certain known frequency ranges for common applications may be indicated, e.g., approximately 20-150 Hz for human heart sounds, approximately 150-1200 Hz for most human lung sounds.

As just noted, the frequency manipulation software described above might function by amplifying certain sound frequencies relative to others, or by limiting or eliminating certain undesired sound frequencies. Any of the these techniques will be referred to herein in as "augmentation" or "augmenting" certain sound frequencies.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

The invention claimed is:

1. A device, comprising:
an acoustic collector configured to collect sound;
an electronic device configured to be removably attached to the acoustic collector, the electronic device comprising a front surface and a back surface opposite to the front surface, the electronic device comprising an electronic screen on the front surface;
a hollow tube that transmits sound waves from a location external to the back surface to a portion of the electronic device when the electronic device is attached to the acoustic collector, wherein at least a portion of the acoustic collector extends rigidly from the back surface and traversing the back surface when the electronic device is attached to the acoustic collector; and
a diaphragm adjacent to an end of the hollow tube that is away from the electronic device.

2. The device of claim 1, wherein the acoustic collector comprises a stethoscope.

3. The device of claim 1, wherein
the electronic device comprises a camera; and
the back surface comprises an aperture exposing the camera.

4. The device of claim 1, wherein:
the electronic screen faces a first direction;
the acoustic collector extends in a second direction when the electronic device is attached to the acoustic collector; and
the first direction and the second direction are opposite directions.

5. The device of claim 1, wherein the acoustic collector extends in a direction with respect to the electronic device that is opposite to the electronic screen.

6. The device of claim 1, wherein an entirety of the acoustic collector is rigid relative to the electronic device when the electronic device is attached to the acoustic collector.

7. The device of claim 1, wherein the electronic device is configured to be removably attached to the acoustic collector via snap-fitting.

8. The device of claim 1, wherein the electronic device is configured to be removably attached to the acoustic collector at a center of the back surface.

9. The device of claim 1, wherein
the acoustic collector extends in a direction when the electronic device is attached to the acoustic collector; and
the direction is perpendicular to the back surface.

10. The device of claim 1, wherein
the electronic device is configured to be removably attached to an acoustic collector at a connection interface; and
the connection interface comprises an opening configured to receive a portion of the acoustic collector.

11. The device of claim 10, wherein the back surface comprises an aperture located at a location different from a location of the connection interface.

12. A method for providing a device, comprising:
providing an acoustic collector configured to collect sound; and
providing an electronic device configured to be removably attached to the acoustic collector, the electronic device comprising a front surface and a back surface opposite to the front surface, the electronic device comprising an electronic screen on the front surface;
providing a hollow tube that transmits sound waves from a location external to the back surface to a portion of the electronic device when the electronic device is attached to the acoustic collector, wherein at least a portion of the acoustic collector extends rigidly from the back surface and traversing the back surface when the electronic device is attached to the acoustic collector; and
providing a diaphragm adjacent to an end of the hollow tube that is away from the electronic device.

13. A device, comprising:
an acoustic collector configured to collect sound;
an electronic device configured to be removably attached to the acoustic collector, the electronic device comprising a front surface and a back surface opposite to the front surface, the electronic device comprising an electronic screen on the front surface;
a hollow tube that transmits sound waves from a location external to the back surface to a portion of the electronic device when the electronic device is attached to the acoustic collector, wherein the hollow tube comprises a collector hole, the collector hole opens in a first direction opposite to a second direction, the electronic screen facing the second direction when the electronic device is attached to the acoustic collector; and
a diaphragm adjacent to an end of the hollow tube that is away from the electronic device.

* * * * *